United States Patent [19]

Kleintjens et al.

[11] Patent Number: 4,539,425
[45] Date of Patent: Sep. 3, 1985

[54] PROCESS FOR THE PREPARATION OF BENZOIC ACID

[75] Inventors: Ludovicus A. L. Kleintjens, Stein (L.); Hubertus M. J. Grooten, Simpelveld, both of Netherlands

[73] Assignee: Stamicarbon B.V., Geleen, Netherlands

[21] Appl. No.: 564,198

[22] Filed: Dec. 22, 1983

[30] Foreign Application Priority Data

Jan. 3, 1983 [NL] Netherlands .......................... 8300008

[51] Int. Cl.$^3$ ............................................ C07C 51/255
[52] U.S. Cl. .................... 562/412; 562/415; 562/494
[58] Field of Search ................. 562/412, 415, 494

[56] References Cited

U.S. PATENT DOCUMENTS

| 1,380,277 | 5/1921 | Weiss et al. | 562/415 |
| 1,686,913 | 10/1927 | Jaeger | 562/494 |
| 1,851,361 | 3/1932 | Jaeger | 562/415 |

*Primary Examiner*—Paul J. Killos
*Attorney, Agent, or Firm*—Cushman, Darby & Cushman

[57] ABSTRACT

Benzoic acid is prepared by oxidation of toluene with an oxygen containing gas, the process is characterized in that the oxidation reaction product is subjected to an extraction with a gas of which the critical temperature is lower than 435 K, this being effected by passing it during at least 1 minute over or through the oxidation reaction product at a flow rate of at least 1 m$^3$ gas per hour per kg of benzoic acid at a temperature of 285-340 K and at a pressure of at least 3 MPa.

8 Claims, No Drawings

PROCESS FOR THE PREPARATION OF BENZOIC ACID

The invention relates to a process for the preparation of benzoic acid by oxydation of toluene with gas containing molecular oxygen.

This oxidation may take place both in the gas phase and in the liquid phase.

In the gas-phase oxidation of toluene to benzoic acid it is preferred to use temperatures of 450–700 K. and pressures of 50–2000 kPa. Such a process for the preparation of benzoic acid by gas-phase oxidation of toluene is known from the European patent application laid open for public inspection No. 40452.

In the liquid phase oxidation of toluene to benzoic acid it is preferred to use temperatures of 390–500 K. and pressures of 200–2000 kPa. This liquid phase oxidation may take place in the presence of a solvent, for instance an aliphatic carboxylic acid, in particular acetic acid, and/or in the presence of a halogen-containing substance acting as promotor, but in view of corrosion problems this oxidation by preference takes place in the absence of an aliphatic carboxylic acid and in the absence of a halogen-containing substance acting as promotor. Such a process for the preparation of benzoic acid by liquid phase oxidation of toluene is known from U.S. Pat. No. 4,339,599.

A major drawback of these known processes for the preparation of benzoic acid is that the reaction product formed in the oxidation contains a rather large amount of impurities, and with the methods currently known for this it is difficult to separate at least a substantial portion of these impurities from the benzoic acid. One of the impurities that is most difficult to remove is diphenyl oxide (DPO).

The object of the invention is to provide a process for the preparation of benzoic acid in which said reaction product is in a simple manner purified from said impurities, in particular from diphenyl oxide.

The invention therefore relates to a process for the preparation of benzoic acid by oxidation of toluene with gas containing molecular oxygen, which process is characterized in that the oxidation reaction product formed is in a solid or liquid form subjected to an extraction with a gas or gas mixture of which the critical temperature is lower than 435 K., such as $SO_2$, $N_2O$, $NO_2$, $NO$, $CO$, $CH_4$, $N_2$, $CO_2$ and ethylene and those mixtures, of these gases among themselves and/or with less than 50 vol.-% of other gases, of which the critical temperature is lower than 435 K., preference being given to $CO_2$, ethylene or mixtures of these two gases, which extraction is effected by passing this gas or gas mixture over or through the oxidation reaction product during at least 1 minute and by preference at most 500 minutes, and in particular 5–50 minutes, at a flow rate of at least 1 m$^3$ (NTP) and by preference less than 500 m$^3$ (NTP), and in particular 5–200 m$^3$ (NPT), gas per hour per kg benzoic acid at a temperature of 285–340 K. and a pressure of at least 3 MPa and by preference below 300 MPa and in particular 5–100 MPa.

The process according to the invention will be elucidated by the following, non-limiting examples. The starting material used in the examples was benzoic acid flakes with a free surface of 2 m$^2$ per g and with an impurity content, relative to the total weight, of 0.02 wt.-% diphenyl oxide (DPO), 0.02 wt.-% 2-methyldiphenyl (2-MDP) and 0.16 wt.-% of 3-methyldiphenyl and 4-methyldiphenyl combined (3- and 4-MDP).

EXAMPLE I

An amount of 13 g benzoic acid flakes was introduced into an aluminum tray. Subsequently, $CO_2$ was during 15 minutes passed over these benzoic acid flakes, the flow rate being 125 m$^3$ (NTP) gas per kg benzoic acid per hour, at 293 K. and 9.5–10.5 MPa.

Subsequently the extracted benzoic acid flakes were analysed. The analysis showed that, relative to its total weight, the purified benzoic acid still had a content of 3- and 4-MDP of only 0.06 wt. %, while the other impurities, including the DPO, were no longer present in detectable amounts.

EXAMPLE II

An amount of 14 g benzoic acid flakes was introduced into a sieve. Subsequently, $CO_2$ was during 15 minutes passed over these benzoic acid flakes, the flow rate being 160 m$^3$ (NTP) gas per kg benzoic acid per hour, at 294 K. and 9.5–10.5 MPa.

Subsequently, the extracted benzoic acid flakes were analysed. The analysis showed that, relative to its total weight, the purified benzoic acid still had a 3- and 4-MDP content of only 0.05 wt.-%, while the other impurities, including the DPO, were no longer present in detectable amounts.

EXAMPLE III

An amount of 22 g benzoic acid flakes was ground to a powder with a free surface of 50 m$^2$/g. Next, the powder thus obtained was placed in a column. Subsequently, $CO_2$ was during 15 minutes passed through the powder, the flow rate being 26 m$^3$ (NTP) gas per kg benzoic acid per hour, at 294 K. and 19–21 MPa.

The extracted benzoic acid powder was subsequently analysed. The analysis showed that, relative to the total weight, the purified benzoic acid still had a 3- and 4-MDP content of only 0.05 wt.-%, while the other impurities, including the DPO, were no longer present in detectable amounts.

EXAMPLE IV

An amount of 21 g benzoic acid flakes was ground to a powder with a free surface of 50 m$^2$/g. Next, the powder thus obtained was introduced into a column. Subsequently, $CO_2$ was during 15 minutes passed through the powder, the flow rate being 30 m$^3$ (NTP) gas per kg benzoic acid per hour, at 294 K. and 24–26 MPa.

The extracted benzoic acid powder was subsequently analysed. The analysis showed that, relative to its total weight, the purified benzoic acid still had a 3- and 4-MDP content of only 0.05 wt.-%, while the other impurities, including the DPO, were no longer present in detectable amounts.

EXAMPLE V

An amount of 23 g benzoic acid flakes was ground to a powder with a free surface of 50 m$^2$/g. The powder thus obtained was introduced into a column. Subsequently, $CO_2$ was during 30 minutes passed over these benzoic acid flakes, the flow rate being 30 m$^3$ (NTP) gas per kg benzoic acid per hour, at 294 K. and 24–26 MPa.

The extracted benzoic acid powder was subsequently analysed. The analysis showed that, relative to its total weight, the purified benzoic acid still had a 3- and 4-MDP content of only 0.04 wt.-%, while the other impurities, including the DPO, were no longer present in detectable amounts.

EXAMPLE VI

An amount of 23 g benzoic acid flakes was ground to a powder with a free surface of 50 m$^2$/g. The powder thus obtained was introduced into a column. Subsequently, $CO_2$ was during 25 minutes passed through the powder, the flow rate being 30 m$^3$ (NTP) gas per kg benzoic acid per hour, at 323 K. and 24–26 MPa.

The extracted benzoic acid powder was subsequently analysed. The analysis showed that, relative to its total weight the purified benzoic acid still had a 3- and 4-MDP content of only 0.03 wt.-%, while the other impurities, including the DPO, were no longer present in detectable amounts.

EXAMPLE VII

An amount of 29 g benzoic acid flakes was introduced into a column. Subsequently, ethylene was during 60 minutes passed along these benzoic acid flakes, the flow rate being 34 m$^3$ (NPT) gas per kg benzoic acid per hour, at 294 K. and 950–1050 kPa.

The extracted benzoic acid flakes were subsequently analysed. The analysis showed that, relative to its total weight, the purified benzoic acid still had an impurity content of only 0.08 wt.-%.

We claim:

1. In a process for the preparation of benzoic acid by the oxidation of toluene in the presence of a gas containing molecular oxygen yielding a reaction product containing impurities, the improvement essentially comprising extracting impurities from said reaction product, in solid or liquid form, with an extraction gas essentially consisting of at least one gas having a critical temperature lower than 435 K., by passing said extraction gas over or through said reaction product at a flow rate of at least 1 m$^3$ (NTP) gas per hour per kg benzoic acid for a time period of at least one minute, at a temperature within the range of between about 285 and 340 K. and at a pressure of at least 3 MPa.

2. The process of claim 1 wherein said extraction gas is selected from the group consisting of $CO_2$, and a mixture thereof.

3. The process of claim 1 wherein said extraction gas is passed over or through said reaction product for a period of between about 1 and 500 minutes.

4. The process of claim 3 wherein said extraction gas is passed over or through said reaction product for a period of between about 5 and 50 minutes.

5. The process of claim 1 wherein the flow rate of said extraction gas is between about 10 and 500 m$^3$ (NTP) gas per hour per kg benzoic acid.

6. The process of claim 1 wherein the flow rate of said extraction gas is between about 5 and 200 m$^3$ (NTP) gas per hour per kg benzoic acid.

7. The process of claim 1 wherein said extraction is carried out at a pressure of between about 3 and 300 MPa.

8. The process of claim 7 wherein said extraction is carried out at a pressure of between about 5 and 100 MPa.

* * * * *